United States Patent
Lavi

(10) Patent No.: US 8,915,421 B2
(45) Date of Patent: Dec. 23, 2014

(54) TRANSFER, LINK, BIND, SPECIMEN TUBE BARCODE INFORMATION TO RFID SPECIMEN TRANSPORT PUCK IN A CONTINUOUS MOVING BINDING PROCESS METHOD

(75) Inventor: Lear Sirous Lavi, Dana Point, CA (US)

(73) Assignee: Lear Sirous Lavi, Laguna Niguel, CA (US)

( * ) Notice: Subject to any disclaimer, the term of this patent is extended or adjusted under 35 U.S.C. 154(b) by 146 days.

(21) Appl. No.: 12/855,697

(22) Filed: Aug. 13, 2010

(65) Prior Publication Data

US 2012/0037696 A1 Feb. 16, 2012

(51) Int. Cl.
*G06F 17/00* (2006.01)
*G06K 19/077* (2006.01)

(52) U.S. Cl.
CPC ............................. *G06K 19/07716* (2013.01)
USPC ....... 235/375; 235/376; 235/475; 235/462.01

(58) Field of Classification Search
CPC ..... G06F 17/00; G06F 17/30879; G06F 7/00; G06K 15/00; G06K 7/00; G06K 7/04; G06K 13/00
USPC ......... 235/375, 376, 383, 438, 446, 475, 476, 235/462.01
See application file for complete search history.

(56) References Cited

U.S. PATENT DOCUMENTS

| | | | |
|---|---|---|---|
| 5,623,415 A * | 4/1997 | O'Bryan et al. | 700/225 |
| 6,343,690 B1 * | 2/2002 | Britton et al. | 198/867.06 |
| 6,363,687 B1 * | 4/2002 | Luciano et al. | 53/55 |
| 6,599,476 B1 * | 7/2003 | Watson et al. | 422/63 |
| 7,748,199 B2 * | 7/2010 | Sankaran et al. | 53/411 |
| 7,837,199 B2 * | 11/2010 | Craig et al. | 277/377 |
| 2007/0254277 A1 * | 11/2007 | Scrabeck et al. | 435/4 |
| 2009/0133363 A1 * | 5/2009 | Guttinger et al. | 53/251 |
| 2010/0089803 A1 * | 4/2010 | Lavi et al. | 209/546 |

* cited by examiner

*Primary Examiner* — Edwyn Labaze

(57) ABSTRACT

The present invention relates generally to the process method of transferring/linking/binding specimen tube label barcode information (such as unique accession number along with other useful laboratory information such as test code information, testing department, specimen temperature) using an RFID Specimen Transport Puck moving continuously on a continuously moving conveyor belt and an RFID Reader/Writer that writes the information onto the RFID chip on the RFID Specimen Transport Puck. The process method is to space the specimen transport pucks on the conveyor, rotate the specimen transport puck that is holding the specimen tube with the barcode while the specimen is moving continuously forward using rotating wheels on the side of the conveyor belt and using a dispersed barcode reader to read the barcode information from the specimen tube label, and to transfer/link/bind the information from the specimen tube barcode label to the RFID chip on the specimen transport puck holding the specimen tube using an RFID reader/writer beneath the conveyor belt, a PLC and a database server.

20 Claims, 5 Drawing Sheets

TRANSFER, LINK, BIND, SPECIMEN TUBE BARCODE INFORMATION TO RFID SPECIMEN TRANSPORT PUCK IN A CONTINUOUS MOVING BINDING PROCESS METHOD

FIELD OF THE INVENTION

The present invention relates generally to the process method of transferring/linking/binding specimen tube label barcode information (such as unique accession number along with other useful specimen information such as test code information, testing department, specimen temperature) using an RFID Specimen Transport Puck moving continuously on a continuous moving conveyor belt and an RFID Reader/Writer that writes the information onto the RFID chip in the RFID Specimen Transport Puck. The process method is to space the specimen transport pucks in a continuous moving process before entering the barcode reading station. Rotate the specimen transport puck that is holding the specimen tube with the barcode label while the specimen transport puck is continuously moving forward. Read the barcode information using a dispersed barcode reader while the specimen is moving continuously forward using rotating wheels on the side of the conveyor belt and a barcode reader. Transfer/link/bind the barcode information to the RFID chip in the specimen transport puck using an RFID reader/writer while the specimen transport puck is continuously moving forward on the conveyor belt.

BACKGROUND OF THE INVENTION

The following background is provided to assist in understanding the invention. Specimens (biological material such as blood, urine, tissues) are obtained from patients and routinely placed in tubes, vials or other collection apparatus and sent to testing laboratories to obtain test results that are reported back to the patient generally through a physician for medical decision making for a patient.

Larger specimen testing laboratories receive a variety of specimens in a variety of types of test tubes (or vials) in a variety of test tube sizes (or vial sizes). These laboratories generally have a specimen processing department that get the specimens ready for the laboratory testing areas. The specimen processing department generally places the specimen into the lab information system (LIS) by creating a specimen identification number in the LIS and a barcode label with the specimen identification on the specimen tube that is used to track the specimen and report the testing results back to the patient. These laboratories generally have many testing instruments (number and variety) that are located over a large square foot facility. The facility is generally segmented into laboratory departments based on the tests and instruments. It is extremely difficult (if not impossible) to have conveyors moving specimen samples to all the various instruments over the large area of the laboratory departments and facility.

Many specimens need to be sorted into particular testing groups in the specimen processing department (example: test code) and hand carried to the particular instrument group performing the testing in the individual testing departments. The specimens are hand sorted to groups or test codes. This requires many resources to perform the hand sorting.

Once the specimens are hand sorted, they are generally hand wanded (the information related to the tube is obtained from the specimen barcode through a barcode reader and placed in a batch or to a location for tracking) and taken to lab area and particular instrument for testing. (The process of hand wanding specimens from the barcode is very labor intensive and requires many resources to perform this task)

The wanded specimens are generally hand wanded to a rack position (operator hand wands the specimen from the barcode label on the tube through a barcode reader and places the specimen in a particular location on a rack so that the specimen can be located later) for tracking. The racks vary is size based on the volume of tests that are to be performed and the batch size for the instrument performing the test. Many racks only have a few specimens wanded to the rack that is taken to the lab and blank positions remain on the fixed racks that are taken to the departments and instruments. (The hand wanding and racking of specimens is very labor intensive and requires many resources to perform this task)

The racked specimens are then generally transported to the labs and instruments on carts. The carts hold various racks with some racks containing only a few specimens for testing. (The racking of specimens are very inefficient and require many racks that do not utilize the full rack size. Many racks are delivered to the departments with only a few specimens on the rack. The rack is not utilized efficiently and it occupies a large amount of space in the labs)

Once the specimens are transported to the labs and instruments on carts, the lab operators generally build testing batches from the specimens. The batches generally contain controls (low and/or medium and/or high target standards that are used to verify that the instrument is testing the batch properly) and may contain repeats (specimens that are re-tested) from prior testing batches. The specimens on the testing batches are generally hand wanded to the batch location for tracking and proper reporting of test results. Some specimens are run on instruments that do not need batching as the volume allows for more continuous flow or the instrument wands the specimens as they are tested. In these cases the specimens are sometimes hand wanded in the department to identify the location of the specimen prior to testing for tracking purposes. Tracking is critical for specimens in a laboratory to reduce the likelihood that a specimen will be lost. Lost specimens is a critical metric that all labs track. A lost specimen generally requires that a patient have the specimen redrawn. For some specimens this is impossible since the specimens are irreplaceable. (The hand wanding of specimens from the barcode label on the specimen tube with a barcode reader in the laboratory prior to testing is extremely labor intensive are requires many laboratory operator resources to perform this task)

Most laboratories have manual specimen processing departments that are described above. In some laboratories that have automated specimen processing areas, sorting is done by robots or other sorting systems. Some of the specimens in test tubes or other container apparatus are sometimes moved on a conveyor using a specimen holding device. His holding device is sometimes called a 'puck'. The 'puck' is generally used to move samples of a specimen type that is going to one specific instrument type for testing. The 'puck' or other holding device will generally move the specimen sample in the tube to a particular instrument for patient result testing. Laboratory workers place the specimens on the pucks while they move on the conveyor belt. The specimens move on the conveyor to a particular specimen testing instrument where the specimen is used in providing a patient test result.

After the specimen is removed from the tube and used in the testing process, a laboratory worker or robot removes the specimen tube from the 'puck' on the conveyor and the 'puck' generally loops around so that a laboratory worker can reload the now empty 'puck' with a new specimen tube. These puck applications are very limited to only very limited instruments that are performing very limited numbers of patient tests. Sorting is only to a few instruments and the instruments are continuous feed high volume flow instruments that do not have batched specimens for testing. The specimen is generally sorted by the barcode on the tube through a barcode reader station that is placed on the conveyor. The puck is rotated at each sort location and the barcode is read. If the specimen can be tested at the particular instrument, the specimen in the puck is directed to the instrument with a gate on the conveyor. These systems can generally sort only to a few instruments and are very expensive and complex.

'Pucks' generally do not have RFID chips in them used to hold information related to the specimen sample it is carrying. 'Pucks' are generally not used to sort samples by particular testing group or test code. 'Pucks' generally do not form into racks that can be carried to various lab areas and instruments for testing. 'Pucks' are generally not used for high speed and high density sorting (sorting to many different sorting locations that are required for larger or mid sized laboratories that have many different instruments and tests to perform) of specimens. 'Pucks' are generally not small in diameter. 'Pucks' generally have many pieces that are assembled to make them costly to manufacture and produce.

Once the specimen is sorted by the robot or other sorting systems, the process of wanding, racking, transporting, and tracking the specimens is manual and is the same as described above for the non-automated specimen processing department laboratories.

Current binding stations have mechanical systems and electrical sensors to locate specimen pucks on the conveyor and hold them fixed on the conveyor belt while holding the pucks and allowing 1 specimen puck into the barcode reading position at a time.

Current binding stations have mechanical systems and electrical sensors to hold the specimen puck fixed at the barcode reading position and to turn the puck in the fixed position while the barcode from the tube is being read and linked to the RFID unique identification numbers on the chip.

Current binding stations have many mechanical parts and sensors that are difficult to assembly.

Current binding stations have significant down time to maintain all the many mechanical and electronic parts in the station.

Current binding stations are expensive and more costly to manufacture and assemble based on the many mechanical and electrical parts.

Current binding stations have significant maintenance cost and are more costly to maintain because of the more downtime and the more mechanical and electrical parts that are required to maintain the current binding station system Current binding stations have a long binding time because of the time to hold the specimen and rotate the specimen in a fixed position. The mechanical parts must hold the puck, then rotate the puck, then release the puck. This time is lengthy and not continuous.

Current binding stations have a limited capacity and have limited throughput based on the time it takes to bind. This reduced throughput is because of the time it takes to hold the specimen puck and rotate the puck and release the puck.

By having a binding station that is continuous and allows the specimen transport puck to move continuously on a continuous conveyor while the barcode is read on the specimen tube and the information is transferred to the RFID chip in the RFID specimen transport puck. This process method allows for much fewer mechanical and electrical parts, is easier to maintain, is lower in cost to manufacture and assemble and has a fast capacity and throughput based on the continuous process method.

SUMMARY OF THE INVENTION

This invention is for the process method of transferring/linking/binding specimen tube barcode information and other relevant specimen information to an RFID chip in a RFID specimen transport puck carrying the specimen tube in a continuous moving process.

This invention of continuous transferring/linking/binding involves 3 major process method steps. The first step is the spacing of specimen transport pucks on a continuous conveyor belt. The puck carrying the specimen tube should be spaced so that only 1 puck enters the barcode reading area at a time. The second step is the reading of the barcode information from the specimen tube barcode label while the specimen is moving continuously forward on the conveyor belt. The puck is rotated while moving continuously forward so that a dispersed range barcode reader can read the barcode information from the label on the tube. The third step is the linking of the barcode information and other relevant specimen testing information to the RFID chip in the specimen transport puck while the puck is moving continuously on the conveyor belt. The barcode information is written to the RFID chip on the puck by a read/write RFID reader beneath the continuously moving conveyor belt. The reader senses the RFID chip and writes/links the barcode information along with any other relevant specimen information such as test code, department, temperature, as the puck continuously moves over the top of the RFID reader/writer. Once the information is written/linked, the RFID reader verifies that the correct information is on the RFID chip on the puck.

This invention is for a process method of transferring/linking/binding specimen tube barcode information to an RFID specimen transport puck that is efficient and fast. Efficient and fast specimen label barcode linking/binding to the RFID specimen transport puck is critical to the process of sorting, wanding specimens on a continuous conveyor. The linking needs to be fast to maximize the throughput of sorting and wanding on the conveyor system. The process needs to be efficient and low in cost to allow for low cost sorting and wanding. Current specimen linking/binding involves complicated processes where specimen pucks are held in place with mechanical systems while the puck is rotated in a fixed position while the barcode is read from the specimen label. Pucks on the conveyor prior to entering the binding station are also held with mechanical systems that hold the pucks fixed on the conveyor while the 1 puck is held fixed and rotated. These fixed binding stations have many mechanical parts, are costly, have significant binding times and are not continuous.

DETAILED DESCRIPTION OF THE INVENTION

Figure 1:
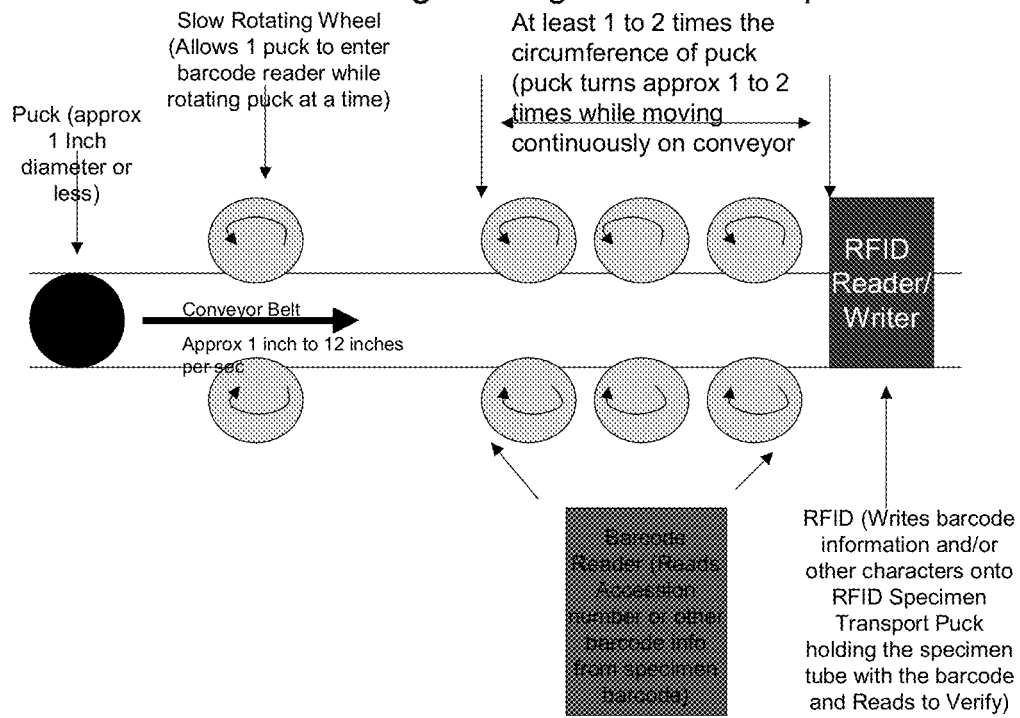
FIG. 1 showing the binding process method with rotating wheels.
Figure 2:
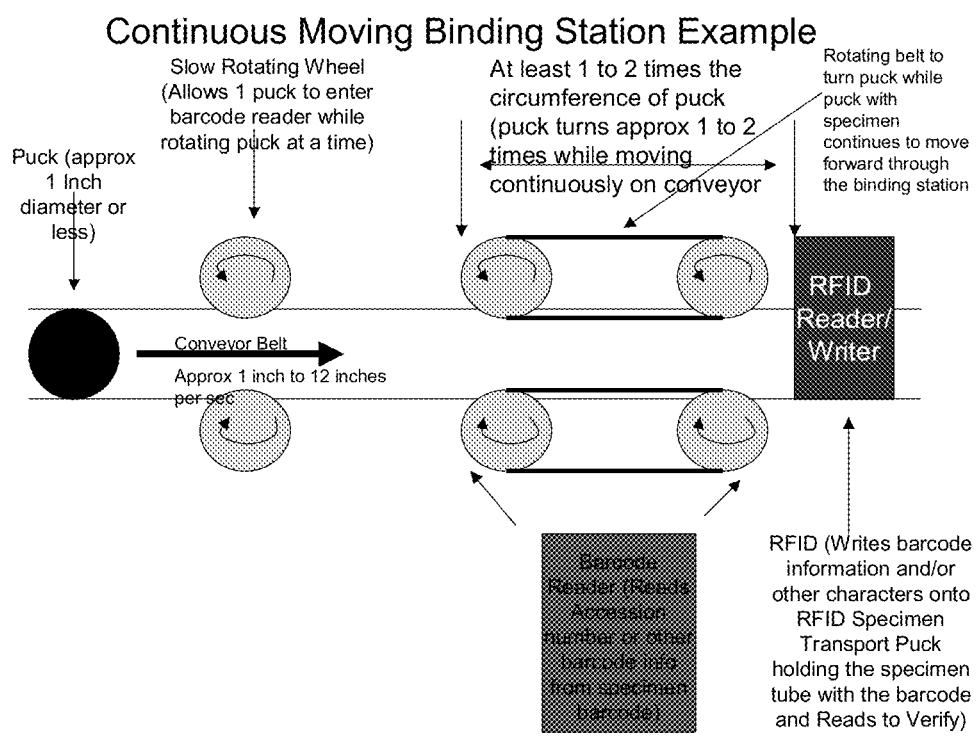
FIG. 2 showing the binding process method with rotating wheels and belt.
Figure 3:
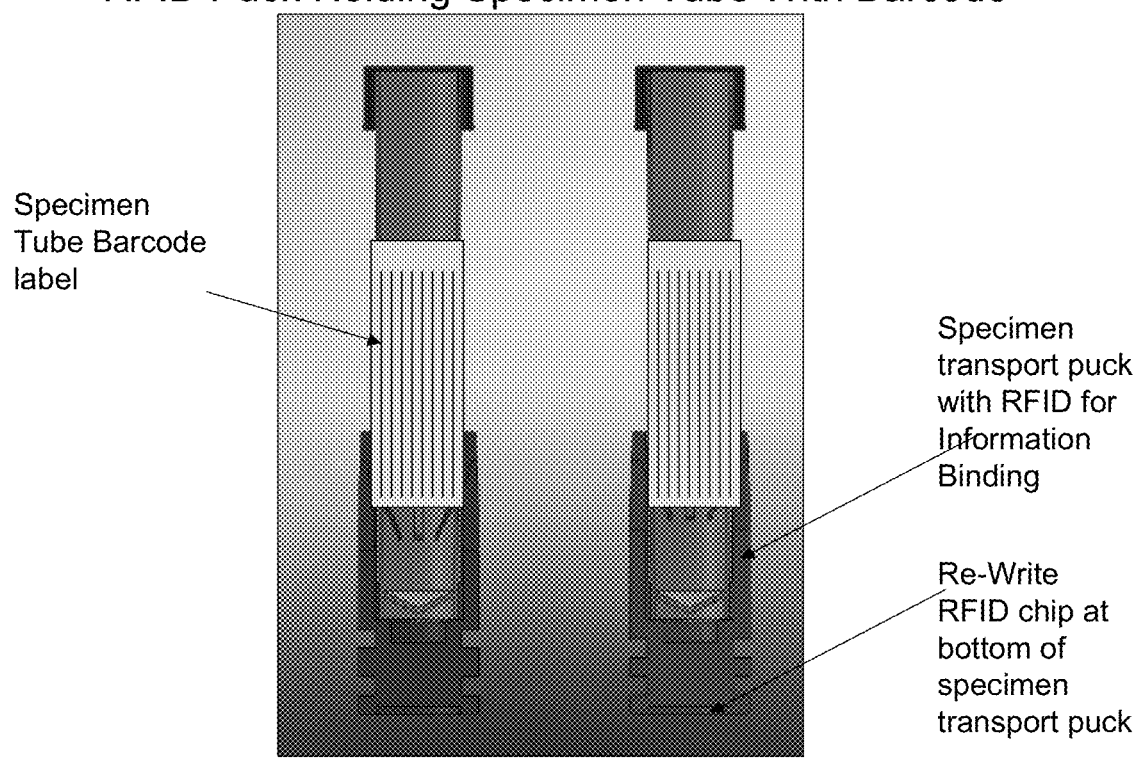
FIG. 3 showing the RFID Specimen Transport Puck holding the specimen tube with barcode label.
Figure 4:
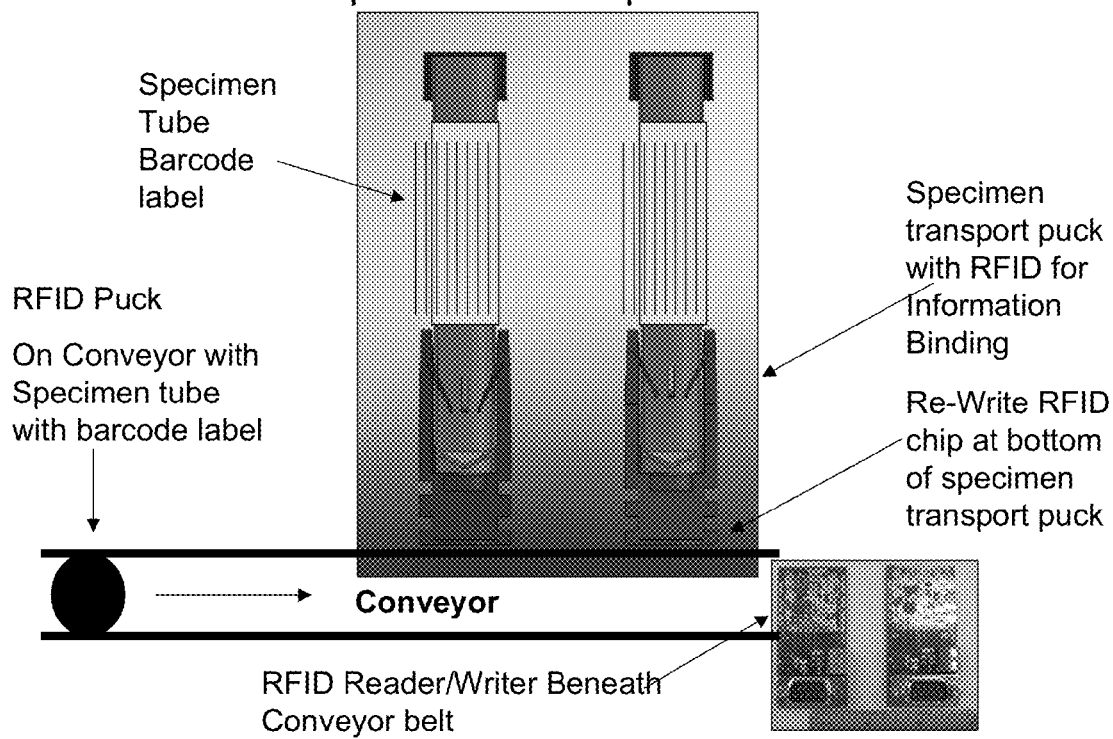
FIG. 4 showing the RFID reader writing barcode information and other matching information to RFID Specimen Transport Puck holding the specimen tube FIG. 5 showing the barcode reader reading the barcode on the specimen tube while the RFID Specimen Transport Puck holding the specimen tube is rotating and moving continuously forward through the binding station.
Figure 5:
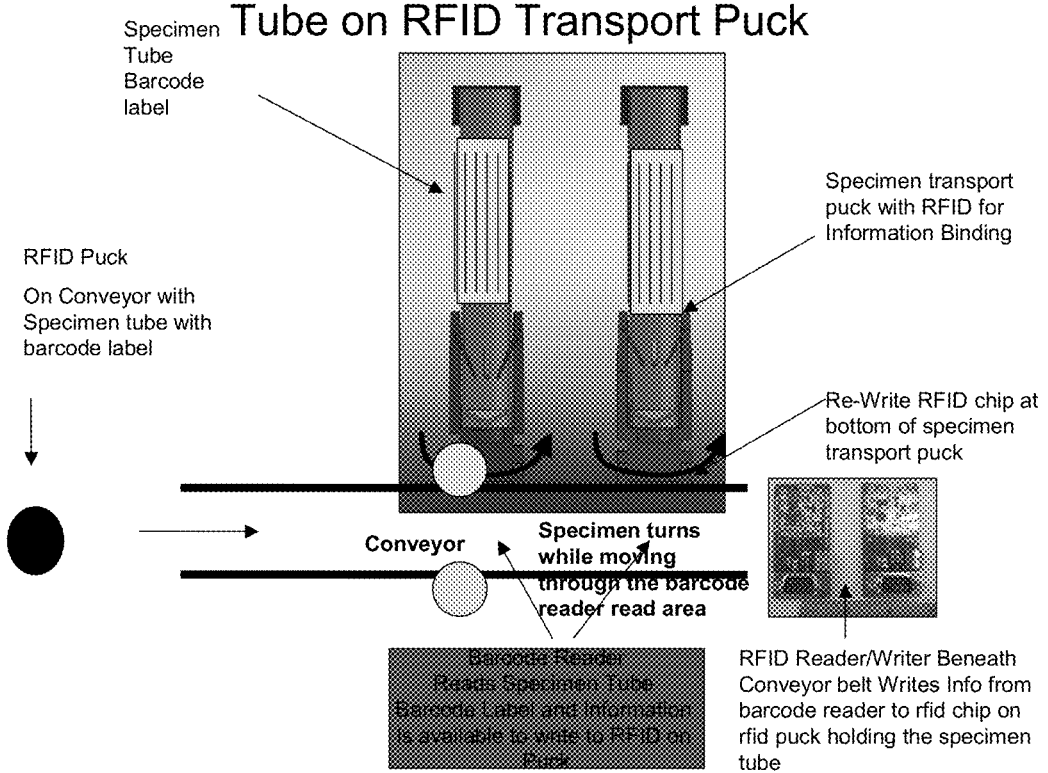

This invention is for the process method of spacing specimen transport pucks in a continuous process on a continuous conveyor.

The puck has a double groove slot design at the lower base of the puck. The specimens tubes are placed in the pucks by an operator that logs the specimen into the laboratory information system. The operator then places the puck with the specimen onto the conveyor. The conveyor has a rail that holds the puck down and centered on the conveyor with the groove slot in the puck. The conveyor then can move the specimen continuously to the sorting locations that run off from the conveyor. Specimens enter onto the conveyor randomly and the spacing of specimen pucks hold the specimen tubes are also random on the conveyor. The specimen pucks must be adequately spaced before being rotated while moving continuously forward through the specimen tube barcode reading process. To perform this adequate spacing of tubes, a wheel is placed on the side of the conveyor ahead of the specimen puck rotating station. The wheel has a variable motor. A wheel can also be placed on the opposite side of the conveyor. It is also possible to have a side plate with springs or just a rail that fits in the groove of the specimen puck on the opposite side of the conveyor. The rotating wheel on the side of the conveyor places pressure on the side of the specimen puck and rotates the puck. The wheel can turn at a very slow rate so that the puck turns slower than the conveyor belt is moving the specimen puck forward. The slow turning wheel applies pressure on the side of the specimen puck while it is rotating, slowing the puck and allowing the puck to slip/slide on the conveyor belt while the conveyor belt skips beneath the specimen puck. This slowing of the specimen puck while rotating the specimen puck forward allows the specimen pucks to be spaced and properly separated. The variable motor will allow the wheel to turn at the speed that is needed to adjust to the proper separation that is required for the specimen puck that is entering the specimen tube barcode reading station while the specimen puck is continuously moving forward.

This invention is for the process method of reading a specimen tube barcode while on a specimen transport puck while the specimen puck is moving continuously in a continuous conveyor.

The puck has an RFID chip located at the bottom of the puck. The RFID chip is re-writeable and has the ability to write information such as the specimen identification, test code, department, temperature (frozen, refrigerated, ambient). The information can be deleted from the RFID chip and new information can be written to the RFID chip on the puck so that it can be reused for sorting, wanding, tracking specimens in the laboratory. The information placed on the RFID is generally from an RFID reader/writer that writes the information after reading the barcode information on the tube. By having the RFID at the bottom of the puck, the information from the tube can be read from the barcode using a barcode reader and then written to the RFID chip through a RFID reader/writer that is beneath the conveyor belt. The barcode information generally contains the specimen identification number and additional information can be written to the chip including the test code that is to be performed on the specimen, the department the specimen is to be taken to for testing, and the temperature the specimen is to be maintained before testing. The specimen transport puck is rotated while moving forward by wheels on the side of the conveyor. The wheels can turn by a variable motor. The wheels can also have a belt stretched across the wheels and turned by one variable motor to one of the wheels. The puck is rotated by the belt that is turning across the wheels on the side of the conveyor. It is possible to have wheels on both sides of the conveyor to rotate the specimen puck. It is also possible to have wheels with belts on both sides of the conveyor to rotate the specimen puck. It is also possible to have wheels and/or wheels with a belt on one side of the conveyor and still rotate the specimen puck while it moves continuously forward. In this case the wheels/belt on the side of the conveyor rotates and places pressure on the side of the specimen puck against a rail and or a spring loaded plate. This allows the specimen puck to rotate by the wheels or belt on one side of the conveyor while the specimen puck moves continuously forward. While the specimen tube with the barcode label is rotated and moving forward, a wide dispersed barcode label reader can read the barcode information from the tube for the transferring/linking/binding to occur with the RFID chip at the bottom of the Specimen Puck. The variable speed motor will allow for the turning of the specimen puck so that the wide dispersed barcode label reader can read the barcode information. The specimen puck can be rotated at a fast speed while moving continuously forward at a fast speed. It is possible to move the specimen puck forward at a faster speed than the conveyor belt that moves the specimen puck on the conveyor. As the specimen puck is rotated forward continuously, it is possible to skip forward and slide forward on the conveyor belt. The rotation length along the conveyor should be at least the circumference length of the specimen puck. The specimen pucks should be separated before entering the barcode reading station where the specimen puck is rotated while moving forward by at least the circumference length of the specimen puck. Only one specimen puck should enter the barcode reading station at a time while the specimen puck is rotating. This will allow reading only one barcode label information to go to the PLC to be used for the RFID reader/writer that is just after the barcode reading station. Once the barcode reading is complete, the information from the barcode is now ready to be transferred/linked/bound to the RFID chip at the bottom of the specimen puck.

This invention is for the process method of transferring/linking/binding the specimen tube barcode information to the RFID chip on the specimen transport puck as the specimen puck moves continuously on a continuous conveyor.

Once the specimen puck is rotated while moving continuously forward on the conveyor and that the barcode information from the specimen tube barcode is read from the wide range barcode reader, the barcode information is ready to be transferred/linked/bound to the RFID chip at the bottom of the specimen puck. Just after the barcode reading station where the specimen puck is rotated, an RFID reader/writer is directly beneath the conveyor belt. The information obtained from the barcode reader is now available from the PLC (program logic controller). The RFID reader/writer senses the RFID chip from the bottom of the specimen puck that has just been read by the barcode reader. The RFID reader/writer then writes the information from the barcode to the RFID chip at the bottom of the specimen puck. The reader can then read the information from the bottom of the RFID chip to verify the correct information is on the chip. This verification can then be sent back to the PLC and on-to the database so that the binding is identified on the server. It is also possible for the RFID reader to read the unique RFID identification information on the chip and send the data to the PLC so that the information can be linked to the barcode information in the database server. Once the transferred/linked information is complete, the overall binding process is complete. The specimen puck with the specimen tube that is carried on the puck is now bound.

The terms and expressions used within this patent have been used in terms of description and are not of limitation and there is no intention in the terms and expressions to exclude any equivalent of the features in the diagrams and descriptions, and recognizes that various modifications are possible and within the scope of this invention claimed.

The invention has been described broadly. Each of the narrower features and specifications fall within the generic disclosure also form part of the invention.

What is claimed:

1. Process method to transfer/link/bind specimen tube label barcode information (unique accession number, test code, department, temperature, etc.) to the RFID chip on the specimen transport puck continuously on a conveyor wherein said process method dramatically reduces the time to transfer/link/bind barcode information and other lab information to the RFID chip on the specimen transport puck since the transfer/link/binding is continuous on the conveyor and wherein said process method dramatically reduces the parts involved in the transferring/linking/binding process.

2. The method of claim 1, wherein process method to read specimen tube label barcode information on a specimen transport puck as the specimen puck moves continuously forward on a conveyor wherein said process method dramatically reduces the time to read the barcode from the label since the puck moves continuously and wherein said process method dramatically reduces the parts involved in the barcode reading.

3. The method of claim 2, wherein the reading of the specimen tube label barcode information includes rotating of the specimen transport puck holding the specimen tube while the specimen transport puck moves continuously forward.

4. The method of claim 2, wherein the reading of the specimen tube label barcode information includes rotating of the specimen transport puck with wheels on the side of the conveyor while the specimen transport puck moves continuously forward on the conveyor wherein the rotation occurs while the specimen puck is moving forward at least the distance of the circumference of the specimen transport puck to allow 1 complete rotation.

5. The method of claim 2, wherein the reading of the specimen tube label barcode information includes rotating of the specimen transport puck with wheels and a belt stretched across the wheels while the transport puck moves continuously forward on the conveyor wherein the rotation occurs while the specimen puck is moving forward at least the distance of the circumference of the specimen transport puck to allow 1 complete rotation.

6. The method of claim 2, wherein the reading of the specimen tube label barcode information includes a dispersed barcode reader wherein the dispersed barcode reader will read the barcode information from the specimen tube label while the tube rotates and moves continuously forward on the conveyor.

7. The method of claim 2, wherein the reading of the specimen tube label barcode information includes a variable speed motor to rotate the specimen transport puck holding the specimen tube while the specimen transport puck moves continuously forward on the conveyor wherein the variable speed motor turns the wheels or belt across the wheels on the side of the conveyor to allow the specimen transport puck to rotate and move at a high speed on the conveyor.

8. The method of claim 2, wherein the reading of the specimen tube label barcode information includes a specimen transport puck with open areas around the specimen transport puck so that the specimen tube label barcode is visible while holding the specimen tube that rotates and moves continuously forward on the conveyor.

9. The method of claim 2, wherein the reading of the specimen tube label barcode information includes rotating wheels on one side of the conveyor to rotate the specimen transport puck while moving continuously forward on the conveyor wherein the rotating wheels press the specimen transport puck against the puck groove on the rail or against a plate with springs on the other side of the conveyor.

10. The method of claim 2, wherein the reading of the specimen tube label barcode information includes rotating wheels with a belt across the wheels on one side of the conveyor to rotate the specimen transport puck and while moving the puck continuously forward on the conveyor wherein the rotating wheels with belt across the wheels press the specimen transport puck against the puck groove on the rail or against a plate with springs on the other side of the conveyor.

11. The method of claim 1, wherein process method to space specimen transport pucks on a conveyor before entering the specimen tube label barcode reading process wherein said process method dramatically reduces the time to space specimen transport pucks on the conveyor since the puck moves continuously and wherein said process method dramatically reduces the parts involved in spacing specimen transport pucks.

12. The method of claim 11, wherein the spacing of specimen transport pucks on a conveyor before entering the specimen tube label barcode reading process is done by a slow turning wheel on the sides of the conveyor wherein the slow turning wheel allows the specimen transport puck to slow down and skip on the conveyor belt and allows proper spacing of the specimen transport pucks.

13. The method of claim 11, wherein the spacing of the specimen transport pucks on the conveyor before entering the specimen tube label barcode reading process has a variable motor turning the wheel on the side of the conveyor wherein the variable motor allows the specimen transport puck to slow down and skip on the conveyor belt and allows proper spacing of the specimen transport pucks.

14. The method of claim 11, wherein the spacing of the specimen transport pucks on the conveyor before entering the specimen tube label barcode reading process has a star wheel on the side of the conveyor wherein the star wheel catches each specimen transport pucks in the grooves of the star wheel wherein the star wheel allows the specimen transport puck to slow down and skip on the conveyor belt and allows proper spacing of the specimen transport pucks.

15. The method of claim 11, wherein the spacing of specimen transport pucks on a conveyor before entering the specimen tube label barcode reading process is done by a slow turning wheel on one side of the conveyor wherein the specimen transport puck is pressed against the specimen transport puck rail or a plate on the opposite side of the conveyor wherein the slow turning wheel allows the specimen transport puck to slow down and skip on the conveyor belt and allows proper spacing of the specimen transport pucks.

16. The method of claim 1, wherein the transferring specimen tube label barcode information (unique accession number, test code, department, temperature, etc.) to the RFID chip on the specimen transport puck continuously on a conveyor using an RFID reader/writer beneath the conveyor belt just after the specimen transport puck is rotated and the specimen tube label barcode information is read.

17. The method of claim 1, wherein the linking specimen tube label barcode information (unique accession number, test code, department, temperature, etc.) to the RFID chip unique identification number on the specimen transport puck continuously on a conveyor using an RFID reader/writer beneath the conveyor belt just after the specimen transport puck is rotated and the specimen tube label barcode information is read.

18. The method of claim 1, wherein the transferring/linking/binding specimen tube label barcode information (unique accession number, test code, department, temperature, etc.) to the RFID chip on the specimen transport puck continuously on a conveyor using a PLC (program logic controller) to transfer/link/bind the tube label barcode information to the RFID chip through the RFID reader/writer.

19. The method of claim 1, wherein the transferring/linking/binding specimen tube label barcode information (unique accession number, test code, department, temperature, etc.) to the RFID chip on the specimen transport puck continuously on a conveyor using a database server to transfer/link the specimen tube label barcode information from the PLC and RFID reader/writer wherein the database server will capture the linking of the specimen transport puck to the specimen tube label barcode wherein the database server is also used to track the specimens throughout the lab testing process wherein the RFID reader/writer can read the RFID chip after writing the information to the chip and verify that the binding data on the RFID chip is correct by comparing to the specimen tube barcode information in the database server.

20. The method of claim 1, wherein the transferring/linking/binding specimen tube label barcode information (unique accession number, test code, department, temperature, etc.) to the RFID chip on the specimen transport puck continuously on a conveyor and a specimen transport puck kick-off on the conveyor belt for specimens transport pucks that do not have the proper binding of the RFID chip information that matches the specimen tube label barcode wherein the specimen transport puck holding the specimen tube is then kicked-off the conveyor using an actuator/sensor/specimen transport puck reject slot.

* * * * *